United States Patent
Kaur et al.

(10) Patent No.: US 12,133,872 B2
(45) Date of Patent: Nov. 5, 2024

(54) METHOD AND SYSTEM FOR EVALUATING AND REDUCING THE DEGREE OF MOSQUITO ATTRACTIVENESS OF INDIVIDUAL

(71) Applicant: Tata Consultancy Services Limited, Mumbai (IN)

(72) Inventors: Harrisham Kaur, Pune (IN); Mohammed Monzoorul Haque, Pune (IN); Sharmila Shekhar Mande, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 389 days.

(21) Appl. No.: 17/808,042

(22) Filed: Jun. 21, 2022

(65) Prior Publication Data

US 2023/0241127 A1 Aug. 3, 2023

(30) Foreign Application Priority Data

Jun. 22, 2021 (IN) .............................. 202121028070

(51) Int. Cl.
*A61K 35/74* (2015.01)
*A61K 35/741* (2015.01)

(52) U.S. Cl.
CPC ............ *A61K 35/74* (2013.01); *A61K 35/741* (2013.01)

(58) Field of Classification Search
CPC ........ G16B 30/00; G16B 40/20; A61K 35/74; A61K 35/741; Y02A 90/10
See application file for complete search history.

(56) References Cited

U.S. PATENT DOCUMENTS 9,578,881 B2 * 2/2017 Zwiebel ............... C07D 405/14
9,839,214 B2 * 12/2017 Goldblum ............. A01N 35/06
(Continued)

OTHER PUBLICATIONS

Cansado-Utrilla, Cintia et al., "The microbiome and mosquito vectorial capacity: rich potential for discovery and translation", Microbiome, Date: May 2021, Publisher: Pubmed, https://microbiomejournal.biomedcentral.com/track/pdf/10.1186/s40168-021-01073-2.pdf.

(Continued)

*Primary Examiner* — An H Do
(74) *Attorney, Agent, or Firm* — Finnegan, Henderson, Farabow, Garrett & Dunner, LLP

(57) ABSTRACT

Mosquito species cause severe and debilitating illnesses. Despite significant advances in clinical medicine, no specific drugs or vaccines are available for diagnosis, treatment, and management of majority of mosquito-borne illnesses. A method and system for evaluating and reducing the degree of mosquito attractiveness of an individual is provided. The methodology involves computation of a metric based on analysis of the host's skin microbial profile and is thus expected to estimate individualized attractiveness profiles. A specific set of bacterial species contributing to skin attractiveness for mosquitoes have been identified and relative abundances of the bacterial species in the identified set have been custom engineered to generate novel features. These features have been utilized for computing an index referred to as a 'Mosquito Attractiveness Quotient (MAQ)' that quantifies or measures the degree of mosquito-attractiveness of individual. The disclosure also proposes formulations that can aid/promote the maintenance of healthy skin microbiota.

14 Claims, 5 Drawing Sheets

Specification includes a Sequence Listing.

(56) References Cited

U.S. PATENT DOCUMENTS 10,768,168 B2 * 9/2020 Ray .................... A01N 35/02
2020/0397732 A1 12/2020 Scott et al.

OTHER PUBLICATIONS

Verhulst, Niels O. et al., "Cultured skin microbiota attracts malaria mosquitoes", Malaria Journal, Date: Dec. 2009, Publisher: Pubmed, https://malariajournal.biomedcentral.com/track/pdf/10.1186/1475-2875-8-302.pdf.
Fernandez-Grandon, G. Mandela et al, "Heritability of Attractiveness to Mosquitoes", Research Article, Date: Apr. 2015, Publisher: Plos One, https://journals.plos.org/plosone/article/file?id=10.1371/journal.pone.0122716&type=printable.

* cited by examiner

METHOD AND SYSTEM FOR EVALUATING AND REDUCING THE DEGREE OF MOSQUITO ATTRACTIVENESS OF INDIVIDUAL

PRIORITY CLAIM

This U.S. patent application claims priority under 35 U.S.C. § 119 to: Indian patent application No. 202121028070, filed on 22 Jun. 2021. The entire contents of the aforementioned application are incorporated herein by reference.

REFERENCE TO SEQUENCE LISTING SUBMITTED ELECTRONICALLY

This application contains a Sequence Listing which has been submitted in ASCII format via EFS-Web and is hereby incorporated by reference in its entirety. The ASCII copy, created on Feb. 22, 2023, is named U.S. Ser. No. 17/808,042_ST25.txt and is 6 KB in size.

TECHNICAL FIELD

The disclosure herein generally relates to the field of analyzing mosquito attractiveness of an individual, and, more particularly, to a method and system to evaluate degree of mosquito-attractiveness of an individual and reduce attractiveness via modulating the skin microbiome of the individual.

BACKGROUND

The tropical and sub-tropical regions around the globe are inhabited by numerous mosquito species that act as vehicles or transmitting agents for a milieu of infectious, disease causing viruses, bacteria, and other kinds of parasites. Mosquito species such as *Aedes, Anopheles, Culex, Haemagogus*, etc., are delivery vectors for microbial pathogens causing severe and debilitating illnesses viz., malaria, dengue, yellow fever, chikungunya, West Nile virus disease, Zika virus disease, filariasis, tularemia, rift-valley fever, Japanese encephalitis, other viral encephalitis, etc. Rapid explosion in population and urbanization, together with expanding global travel, un-paralleled climate change, and large gaps in health infrastructure provide favorable conditions for rapid proliferation and ubiquitous spread of mosquitoes thereby resulting in several kinds of life-threatening disease outbreaks.

Despite significant it advances in clinical medicine and pharmacology, no specific drugs or vaccines are available for diagnosis, treatment, and management of majority of mentioned mosquito-borne illnesses. Hence, to combat the proliferation and spread of infectious disease-causing agents transmitted through mosquitoes, protection from mosquito bites continues to remain as the principal and the most efficacious preventive and prophylactic disease-control strategy against vector borne diseases.

Traditionally, vector-control strategies and approaches employ one or a combination of insecticides/pesticides that deflate mosquito populations by either killing the larvae or the adult form of vectors, or by eliminating the breeding sites of these vectors. Several insecticidal compounds, including, organophosphates, carbamates, pyrethroids, etc., are commercially utilized for this purpose. However, insecticidal resistance, particularly against commonly used pyrethroids, is posing a significant challenge for effective vector control via this route. Furthermore, insecticidal solutions are also reported to exert adverse effects on human health. Further, different species of mosquito vectors transmit different kinds of diseases, having distinct epidemiological characteristics and therefore require discrete (and customized) vector control strategies.

Mosquitoes locate human hosts through an amalgamation of host-specific thermal, visual, and chemical signals. Although, mosquitoes primarily rely on chemo-sensory olfactory cues for precise orientation and landing on human host, palpable and thermal cues, including heat, moisture/humidity, and host's visible silhouette additionally guide the mosquitoes to fly towards the host. Among the chemical cues, carbon dioxide from human exhaled breath and a blend of diverse skin odor-related cues regulate the host-seeking behavior of mosquitoes. The plethora of host-specific skin odors is attributable to certain volatile organic compounds (VOCs), also known as 'sweat metabolites', which are generated by metabolic activities of micro-organisms residing on human skin.

The human skin is an enormous and complex ecosystem, constituting diverse niches inhabited by heterogeneous microbial communities. Trillions of micro-organisms, comprising of, bacteria, viruses, fungi, and archaea, populate the skin surface and together shape the skin microbiota. Physiological factors specific to the host, in particular, age, gender, skin pH, temperature, humidity, oxygen and nutrient availability, sebum and hormone secretion, immune system, and the presence of numerous anatomical skin sites contribute to the temporal variability of the skin flora. Distinct groups of resident skin microbes are capable of biosynthesizing/metabolizing a myriad of VOCs. Given the immense inter-individual variability in skin microbiota, the uniqueness and intensity of skin odor is therefore directly correlated with the relative abundances of certain groups of skin bacteria. The imbalance/dysbiosis in the healthy repertoire of skin microbiota is associated with the range of acute and chronic skin disorders, such as acne, psoriasis, dermatitis, leprosy, rosacea, etc. Furthermore, recent in-vitro and in-vivo studies have shown that VOCs produced by skin bacteria are attractive to malarial parasite transmitting female *Anopheles* mosquito.

SUMMARY

Embodiments of the present disclosure present technological improvements as solutions to one or more of the above-mentioned technical problems recognized by the inventors in conventional systems. For example, in one embodiment, a system for evaluating and reducing the degree of mosquito-attractiveness of an individual is provided. The system comprises a sample collection module, an extraction unit, a sequencer, one or more hardware processors, a memory and an administration module. The sample collection module collecting a biological sample from skin of the individual, wherein the biological sample is representing skin microbiome of the individual. The extraction unit extracts microbial nucleic acid content from the collected biological sample. The sequencer sequences the extracted microbial nucleic acid content, via a sequencer, to get sequence data. The memory is in communication with the one or more hardware processors, wherein the one or more first hardware processors are configured to execute programmed instructions stored in the one or more first memories, to: categorize the sequenced data into a plurality of taxonomic groups utilizing standardized classification algorithms and a plurality of databases; compute raw abundance values of a plurality of features, wherein each feature corresponds to a unique taxonomic group from amongst the plurality of taxonomic groups; normalize and scale the computed raw abundance values of each of the plurality of features, wherein the normalizing is configured to adjust the raw abundance values to a common scale, thereby correcting a bias in the computation of the raw abundance values, wherein the bias is due to a plurality of factors; identify a set of features from the plurality of features based on similarity between a nucleotide sequence corresponding to the feature and the nucleotide sequences corresponding to a set of pre-identified amplicon sequence variants (ASVs), and wherein the set of features is identified if the similarity exceeds a pre-defined range; perform one or more feature engineering techniques on the normalized and scaled abundance values of the set of features to obtain a collated feature table (CFT), wherein the CFT comprises of a plurality of novel engineered features and their corresponding engineered raw abundance values; provide binary classifier utilizing a pre-built classification model; compute a mosquito attractiveness quotient (MAQ) score by feeding the CFT to the binary classifier; and compare the computed MAQ score with a predefined threshold score, to categorize the individual to be one of a highly attractive or a poorly attractive to mosquitoes; and an administration module for administering skin microbe based therapeutic interventions to the individual, if the individual is categorized as highly attractive to mosquitoes, wherein the therapeutic interventions are configured to: combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

In another aspect, a method for evaluating and reducing the degree of mosquito-attractiveness of an individual is provided. Initially, a biological sample is collected from skin of the individual, wherein the biological sample is representing skin microbiome of the individual. Further, microbial nucleic acid content is extracted from the collected biological sample via an extraction unit. The extracted microbial nucleic acid content is then sequenced, via a sequencer, to get sequence data. In the next step, the sequenced data is categorized into a plurality of taxonomic groups utilizing standardized classification algorithms and a plurality of databases. Further, raw abundance values of a plurality of features is computed, wherein each feature corresponds to a unique taxonomic group from amongst the plurality of taxonomic groups. In the next step, the computed raw abundance values of each of the plurality of features are normalized and scaled, wherein the normalizing is configured to adjust the raw abundance values to a common scale, thereby correcting a bias in the computation of the raw abundance values, wherein the bias is due to a plurality of factors. Further a set of features is identified amongst the plurality of features based on similarity between a nucleotide sequence corresponding to the feature and the nucleotide sequences corresponding to a set of pre-identified amplicon sequence variants (ASVs), and wherein the set of features is identified if the similarity exceeds a pre-defined range. One or more feature engineering techniques are then performed on the normalized and scaled abundance values of the set of features to obtain a collated feature table (CFT), wherein the CFT comprises of a plurality of novel engineered features and their corresponding engineered abundance values. In the next step, a binary classifier is provided, wherein the binary classifier utilizing a pre-built classification model. In the next step a mosquito attractiveness quotient (MAQ) score is computed by feeding the CFT to the binary classifier. Further, the computed MAQ score is compared with a predefined threshold score, to categorize the individual to be one of a highly attractive or a poorly attractive to mosquitoes. And finally, skin microbe based therapeutic interventions is administered to the individual, via an administration module, if the individual is categorized as highly attractive to mosquitoes, wherein the therapeutic interventions are configured to: combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

In yet another aspect, there are provided one or more non-transitory machine-readable information storage mediums comprising one or more instructions which when executed by one or more hardware processors cause evaluating and reducing the degree of mosquito-attractiveness of an individual is provided. Initially, a biological sample is collected from skin of the individual, wherein the biological sample is representing skin microbiome of the individual. Further, microbial nucleic acid content is extracted from the collected biological sample via an extraction unit. The extracted microbial nucleic acid content is then sequenced, via a sequencer, to get sequence data. In the next step, the sequenced data is categorized into a plurality of taxonomic groups utilizing standardized classification algorithms and a plurality of databases. Further, raw abundance values of a plurality of features is computed, wherein each feature corresponds to a unique taxonomic group from amongst the plurality of taxonomic groups. In the next step, the computed raw abundance values of each of the plurality of features are normalized and scaled, wherein the normalizing is configured to adjust the raw abundance values to a common scale, thereby correcting a bias in the computation of the raw abundance values, wherein the bias is due to a plurality of factors. Further a set of features is identified amongst the plurality of features based on similarity between a nucleotide sequence corresponding to the feature and the nucleotide sequences corresponding to a set of pre-identified amplicon sequence variants (ASVs), and wherein the set of features is identified if the similarity exceeds a pre-defined range. One or more feature engineering techniques are then performed on the normalized and scaled abundance values of the set of features to obtain a collated feature table (CFT), wherein the CFT comprises of a plurality of novel engineered features and their corresponding engineered abundance values. In the next step, a binary classifier is provided, wherein the binary classifier utilizing a pre-built classification model. In the next step a mosquito attractiveness quotient (MAQ) score is computed by feeding the CFT to the binary classifier. Further, the computed MAQ score is compared with a predefined threshold score, to categorize the individual to be one of a highly attractive or a poorly attractive to mosquitoes. And finally, skin microbe based therapeutic interventions is administered to the individual, via an administration module, if the individual is categorized as highly attractive to mosquitoes, wherein the therapeutic interventions are configured to: combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
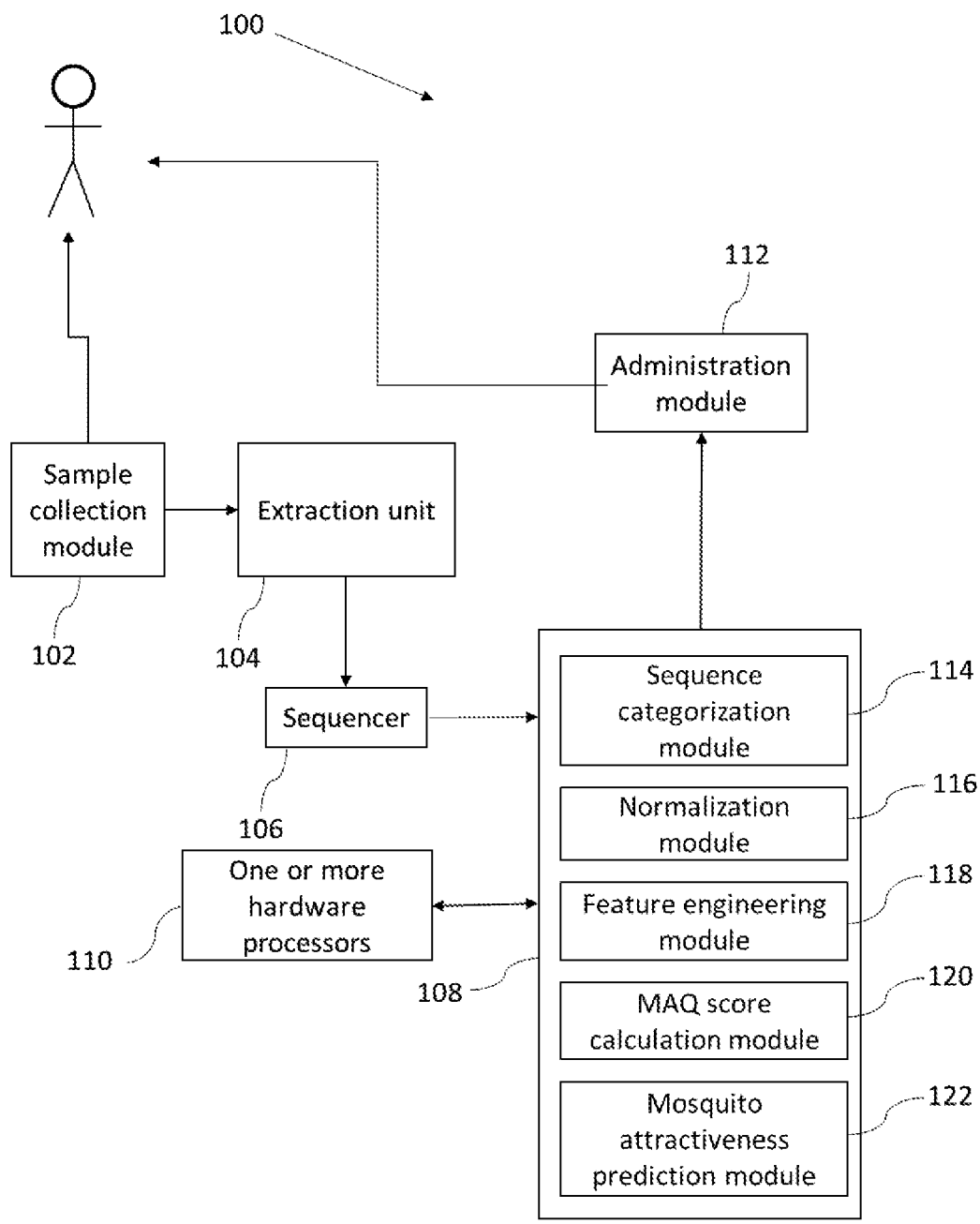
FIG. 1 is a block diagram of a system for evaluating and reducing the degree of mosquito-attractiveness of an individual according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Glossary—Terms Used in the Embodiments

The expression "microbiota" in the context of the present disclosure refers to the collection of microorganisms, such as, bacteria, archaea, protists, fungi, and virus, that inhabit a particular ecological niche (e.g. a human body site such as skin, gut, oral cavity, etc.,) or an environmental/geographical site (e.g. soil surface, air sample, halophilic locations, kitchen table surface, etc.)

The term "microbiome" refers to the collection of genetic material of micro-organisms that reside in a particular geographical niche. The term "pathogen" refers to any organism that can cause disease in a host.

The term "Vector" refers to any organism that transmits infectious pathogens or parasites from one infected organism to another. Examples of common disease-carrying vectors are mosquitoes, ticks, and flies.

The term "vector-borne diseases" refers to infectious diseases transmitted/ferried from one infected host to another through vector organisms. Examples of common vector-borne diseases are malaria, dengue fever, chikungunya, encephalitis, and filariasis etc.

Mosquito species such as *Aedes, Anopheles, Culex, Haemagogus*, etc., are delivery vectors for microbial pathogens causing severe and debilitating illnesses. Despite significant advances in clinical medicine and pharmacology, no specific drugs or vaccines are available for diagnosis, treatment, and management of majority of mentioned mosquito-borne illnesses. Hence, to combat the proliferation and spread of infectious disease-causing agents transmitted through mosquitoes, protection from mosquito bites continues to remain as the principal and the most efficacious preventive and prophylactic disease-control strategy against vector borne diseases.

There are few techniques that exist in the prior art to estimate/define/quantify/evaluate the mosquito attractiveness of an individual. These techniques require in-vitro experiments to quantify/measure the differential attractiveness of different human skin emanations or VOCs (volatile organic compounds), either alone or in combination, towards disease-transmitting mosquito vectors. These experiments not only require expensive and highly specialized equipment, but also need to be carried out under controlled and regulated experimental conditions, with selectively-bred mosquito populations. Although, such experiments are extremely sensitive, spatial and temporal variations in factors, such as, external temperature, wind speed and direction, time of the day, etc., can skew the measurements and lead to spurious results. Moreover, even miniscule heterogeneity in mosquito population densities can result in inaccurate extrapolation of experimental data/results. Further, given the high inter-individual variability between host-skin bacteria, and thus skin odor profiles, deciphering generic odor-producing compounds that can potentially act as a universal magnet/repellent for all pathogen-carrying mosquito species still remains a major challenge.

In addition, numerous volatile chemical compounds that contribute to host odor have been quantified and tested for their degree of attractiveness towards mosquitoes, but none of them have been found to be universally attractive to all species of mosquitoes. Moreover, owing to the rapidly evolving mosquito population, the traditional vector-control strategies may be soon deprived of their efficacies. Hence, the demand of the hour necessitates the design and deployment of novel microbiome-based personalized vector management approaches.

The present disclosure provides a method and system for quantifying the mosquito-attractiveness of an individual based upon the composition and structure of the resident skin microbial community. The method proposed in the present disclosure is independent of above-mentioned confounding factors that are known to complicate and potentially misrepresent the results of in-vitro experiments. The proposed method, in one embodiment, estimates differential attractiveness of an individual to mosquitoes through the collection and analysis of a skin swab sample of the individual. The method of collecting scores over other methods in being relatively simpler, non-invasive/minimally-invasive, and also cost-effective. In addition, the methodology proposed in the present disclosure involves computation of a metric based on analysis of the host's skin microbial profile and is thus expected to estimate individualized attractiveness profiles. This would aid in adoption of personalized screening and therapeutic vector-control options.

Further, the present disclosure provides microbiome-based approach for controlling and minimizing the attractiveness of individuals towards host-seeking mosquitoes. This approach is primarily focused towards targeting the harmful bacterial groups (residing in skin) that are capable of producing attractive VOCs (i.e. those that are attractive to mosquitoes), The targeting (of harmful bacterial groups residing in/on the skin of the individual) is achieved through administering (to the individual) a consortium of microbes or a consortium of microbes in combination with antibiotic drugs. The present disclosure also proposes pre-/pro-/anti-/meta-/post-/syn-biotic formulations that can aid/promote the maintenance of healthy skin microbiota.

A specific set of bacterial species (prevalent in human skin microbiota) contributing to skin attractiveness for mosquitoes have been identified and the relative abundances of the bacterial species in the identified set have been custom engineered to design/generate novel features. These newly designed features have been utilized for computing a novel metric/index referred to as a 'Mosquito Attractiveness Quotient (MAQ)' that quantifies or measures the degree of mosquito-attractiveness of an individual. The 'MAQ' is evaluated based on the taxonomic abundance profile of resident skin microbiota and is indicative of the metabolic/functional potential of skin bacteria to biosynthesize/metabolize certain metabolites that play a role in augmenting/reducing the attractiveness of an individual to host-seeking mosquitoes. The MAQ metric is subsequently used to assess, for the individual, the probabilities/risks (i.e. the attractiveness) of the individual to mosquito bites.

Referring now to the drawings, and more particularly to FIG. 1 through FIG. 3B, where similar reference characters denote corresponding features consistently throughout the figures, there are shown preferred embodiments and these embodiments are described in the context of the following exemplary system and/or method.

According to an embodiment of the disclosure, a block diagram of a system 100 for evaluating and reducing the degree of mosquito-attractiveness of an individual is shown in FIG. 1. The system 100 consists of a sample collection module 102, an extraction unit 104, a sequencer 106, a memory 108, one or more hardware processors (referred as a processor, herein after) 110 and an administration module 112 as shown in FIG. 1. The processor 110 is in communication with the memory 108. The memory 108 further includes a plurality of modules for performing various functions. The plurality of modules comprises a sequence categorization module 114, a normalization module 116, a feature engineering module 118, a Mosquito Attractiveness Quotient (MAQ) score calculation module 120 and a mosquito attractiveness prediction module 122.

The system 100 comprises the extraction unit 104 and the sequencer 106. DNA is first extracted from the microbial cells constituting the probiotic sample or microbiome sample using laboratory standardized protocols by employing the DNA extractor 104. Next, sequencing is performed using the sequencer 106 to obtain the sequenced metagenomic reads. The sequencer 106 performs whole genome shotgun (WGS) sequencing from the extracted microbial DNA, using a sequencing platform after performing suitable pre-processing steps (such as, sheering of samples, centrifugation, DNA separation, DNA fragmentation, DNA extraction and amplification, etc.).

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

According to an embodiment of the disclosure, the skin (microbiome) sample is collected using the sample collection module 102. The sample collection module 102 is configured to obtain a sample from the skin of the individual.

Figure 2A:
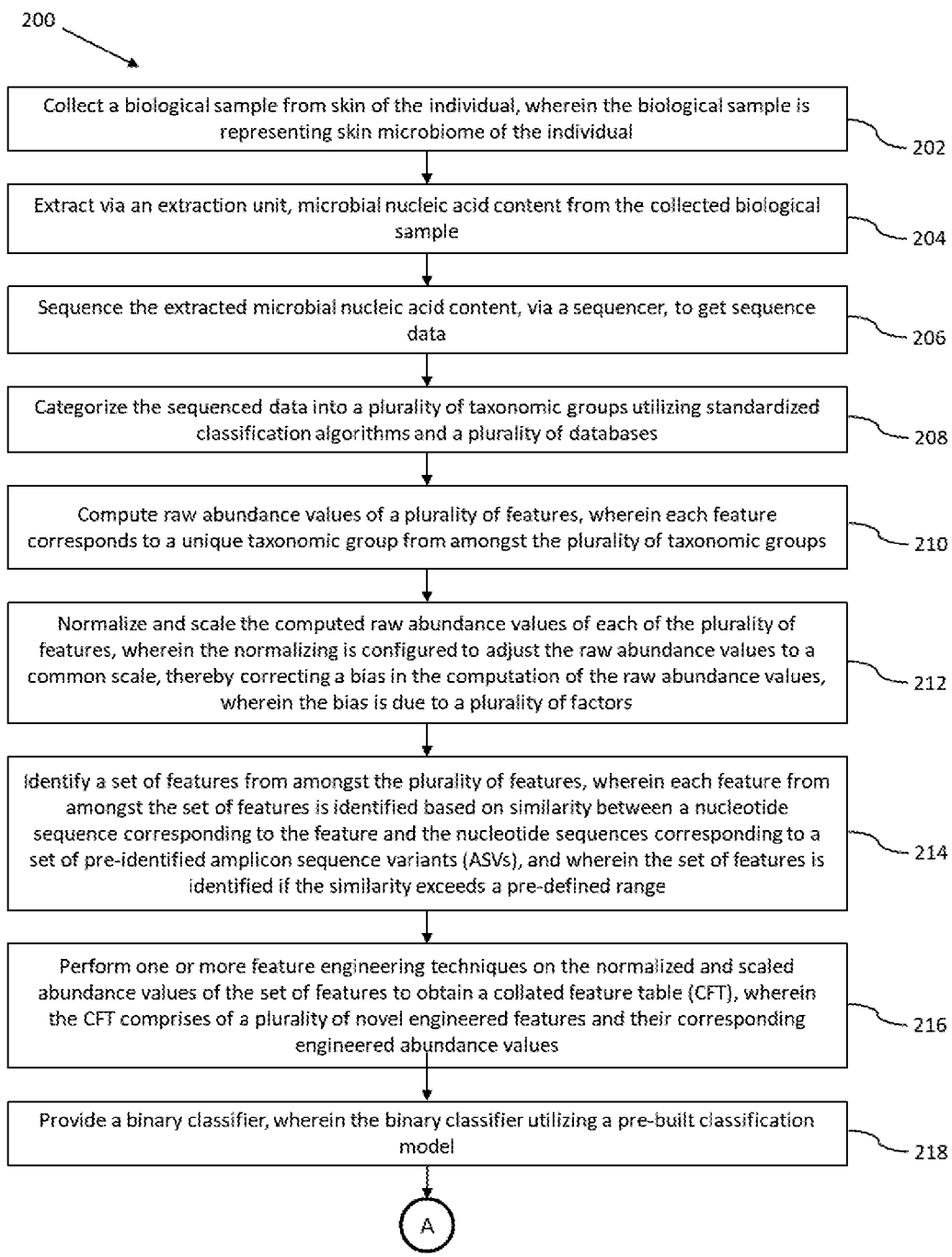
FIGS. 2A and 2B is a flowchart illustrating the steps involved in a method for evaluating and reducing the degree of mosquito-attractiveness of the individual according to some embodiments of the present disclosure.
Figure 2B:
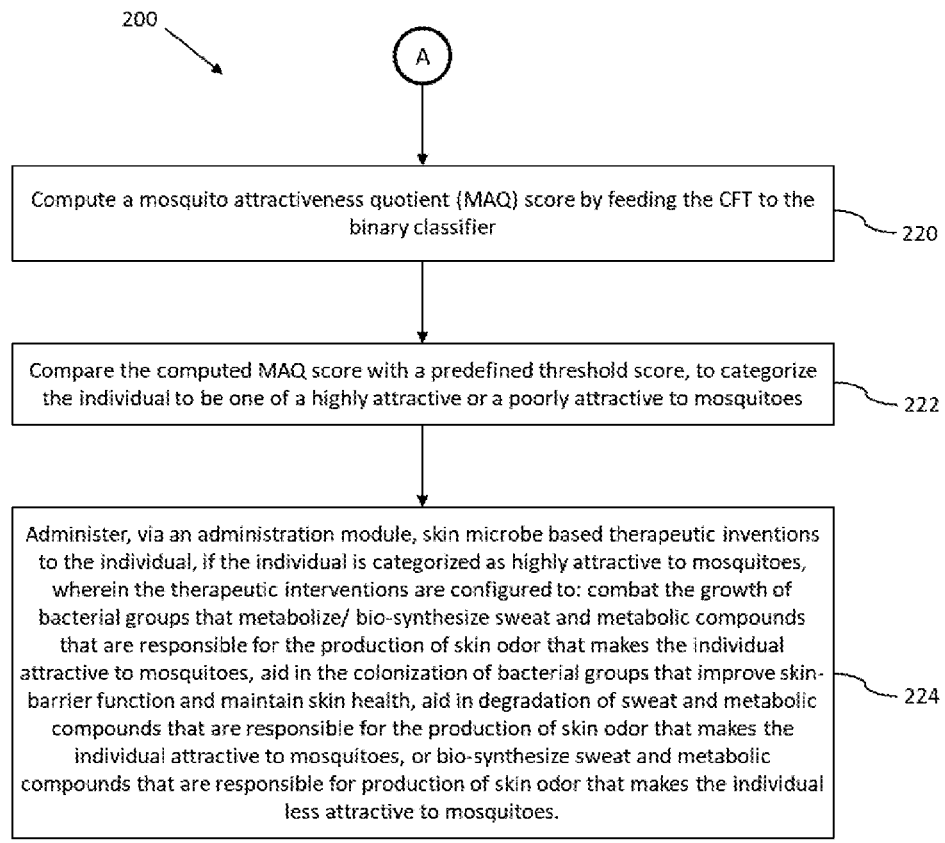

In operation, a flow diagram of a method 200 evaluating and reducing the degree of mosquito-attractiveness of the individual is shown in FIGS. 2A and 2B. The method 200 depicted in the flow chart may be executed by a system, for example, the system, 100 of FIG. 1. In an example embodiment, the system 100 may be embodied in a computing device.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 200 are described with help of system 100. However, the operations of the method 200 can be described and/or practiced by using any other system.

Initially at step 202 of method 200, a biological sample is collected from skin of the individual using the sample collection module 102. The biological sample is representing skin microbiome of the individual. In order to study and evaluate the taxonomic composition of the person's microbiota, skin sample is collected by either swabbing/scraping one or more layers of skin with the help of a sterile scalpel or by repeated rubbing of defined skin sites with a sterile swab. Both the techniques, individually, or in combination can be used to obtain the skin sample for further investigation. In another example, biopsy of the skin tissue obtained from a specified/defined site may also be employed for sample collection. In addition, tape-stripping methods, which sample the components of the upper layer of skin (i.e. stratum corneum) using an adhesive tape are also one of the methods of skin sample collection and are also well within the scope of this disclosure. Further, a cup-scrub sampling technique may also be applied for sample collection. Thus, by appropriately utilizing the above-mentioned sampling methods, either alone or in combination, skin samples from different body skin sites, such as arms, feet, palm, ankles, back of neck and knees, elbows, face, etc., can be obtained.

Further at step 204 of the method 200, microbial nucleic acid content is extracted from the collected biological sample via the extraction unit 104. At step 206 the extracted microbial nucleic acid content is sequenced, via the sequencer 106 to get sequence data. The sequence data comprises of a plurality of sequence reads corresponding to the extracted nucleic acid content of the microbes in the collected biological sample. Microbial nucleic acid content from the collected skin sample is extracted using suitable molecular biology wet-lab protocols. Nucleic acid extraction is performed using standardized laboratory isolation and purification kits, such as, Norgen, Purelink, OMNIgene/Epicenter, etc.

Sequencing of microbial nucleic acid content (which is extracted from the skin sample) is performed using one or more or a suitable combination of molecular biology and wet-lab protocols, including but not limited to, Polymerase Chain Reaction (PCR), quantitative Polymerase Chain Reaction (qPCR), pyrosequencing, Denaturing Gradient Gel Electrophoresis (DGGE), Restriction Fragment Length Polymorphism, microarrays or Next Generation Sequencing (NGS). Nucleic acid hybridization or any other methods that can identify, detect, extract, and sequence microbial nucleic acids present in the collected skin samples are well within the scope of this disclosure. Nucleic acid sequences comprise of DNA, RNA, mRNA, rRNA, etc. In addition, assaying of any protein sequences (other biological components) that may indicate the presence/absence and/or the absolute/specific abundances of all/specific bacteria present in the collected skin sample may also be employed as a procedure. For the assaying/detection/quantification of protein sequences, gel electrophoresis, mass spectroscopy, AQUA, iTRAQ, etc., or any other methods are within the scope of this disclosure.

The above-mentioned sequencing procedures, either alone or in combination, are utilized to sequence the microbial nucleic acid/gene/protein content in human readable (and computer analyzable) form/data formats called reads. Any of the microbial phylogenetic marker genes, such as, 16S rRNA, 23S rRNA, rpoB, cpn60, etc., may be used as a target for amplification and for obtaining respective sequence data. In addition, application of Whole genome sequencing (WGS) to analyze the taxonomic and functional nucleic acid/gene content of entire microbial content in the skin sample is within the scope of this disclosure. RNA sequencing, a technique that characterizes and quantifies the repertoire of active gene transcripts in a sample, may be also be utilized as a method for analyzing the microbial components in the skin sample. The sequence data, thus generated, is subsequently computationally analyzed by employing suitable analysis protocols to estimate/quantify the microbial composition (in both taxonomic and functional terms) of the collected sample.

Further at step 208 of the method 200, the sequenced data is categorized into a plurality of taxonomic groups utilizing standardized classification algorithms and a plurality of databases. The standardized state-of-art classification algorithms and databases classify and assign sequence reads into distinct bacterial groups at various taxonomic levels. Standardized methods such as, methods such as, Naïve Bayesian classifier as implemented in Ribosomal Data Project, that classify microbial sequence reads into taxonomic groups, or methods utilizing sequence based matches with different marker gene databases, such as, Silva, Ribosomal Database Project database can also be applied for analyzing sequence data and estimating the raw counts or abundances of various microbial taxonomic groups/taxonomic units in the collected skin sample. The disclosure also supports the creation of an in-house 16S rRNA database of strains of bacterial genomes for customized analysis. Any other method for identifying the microbial composition of a given sample can also be utilized. It should be noted that the abundances/counts of bacterial groups corresponding to taxonomic levels, such as, but not limited to, kingdom, phylum, class, order, family, genus, species, strains, OTUs (Operating Taxonomic Units), Amplicon Sequence Variants (ASVs) etc. may be considered for analysis. Calculation of counts of microorganisms, other than bacteria in the skin samples, is also within the scope of the disclosure.

At step 210 of the method 200, raw abundance values of a plurality of features is computed, wherein each feature corresponds to a unique taxonomic group from amongst the plurality of taxonomic groups. The unique taxonomic groups are microbial groups present in skin of individuals who are either highly-attractive to mosquitoes or poorly-attractive to mosquitoes.

Further at step 212, the computed raw abundance values of each of the plurality of features are normalized and scaled using the normalization module 116. The normalizing is configured to adjust the raw abundance values to a common scale, thereby correcting a bias in the computation of the raw abundance values, wherein the bias is due to a plurality of factors. The plurality of factors may be variation in sampling techniques, library sizes and other technical discrepancies. Any kind of normalization of bacterial abundance values, including percentage, z-score normalization, cumulative sum scaling, percentile scaling, quantile scaling, Atkinson's log transformation, rarefaction, etc., is within the scope of this disclosure. Further, the count-normalized microbial abundance values are scaled. The 'scaling' step comprises of transforming the microbial abundance values in each sample to represent the abundance in the form of scaled values, wherein the scaling on microbial counts is performed through one or more of the methods, such as, minmax scaling, maxAbs scaling, robust scaling, quantile scaling, percentile scaling, cumulative sum scaling or Atkinson's log-ratio transformation.

In the next step 214 of the method 200, a set of features from amongst the plurality of features is identified. Each feature from amongst the set of features is identified based on similarity between a nucleotide sequence corresponding to the feature and the nucleotide sequences corresponding to a set of pre-identified amplicon sequence variants (ASVs), and wherein the set of features is identified if the similarity exceeds a pre-defined range. For instance, the predefined range in case of a sequence homology search technique is between 80-100 percent sequence identity value. The quantification of similarity is done using one of a plurality of techniques comprising homology search, BLAST searching, Hidden Markov Model based search, Position Specific Scoring matrices (PSSM), and motif search.

Further at step 216 of the method 200, one or more feature engineering techniques are performed on the normalized and scaled abundance values of the set of features to obtain a collated feature table (CFT), wherein the CFT comprises of a plurality of novel engineered features and their corresponding engineered abundance values. This step is performed to engineer novel features that amplifies and better represent the microbial signatures (within the sample) that help in evaluating attractiveness of the individual to mosquito bites. It should be noted that any state-of-art feature engineering methodologies, such as, mathematical transformations, grouping operations, data or feature splitting, data binning, etc. can be adopted to extract meaningful features from raw/normalized/scaled/transformed microbial abundance data. The one or more feature engineering techniques the comprise of applying mathematical transformation on a predefined combinations of the normalized and scaled abundance values corresponding to an identified set of features to obtain novel features and corresponding engineered abundance values.

At step 218, a binary classifier is provided. The binary classifier utilizes a pre-built classification model. The binary classifier is one of a Weighted Logistic regression' (WLR) classifier, random forest classifier, decision trees technique, naive Bayes classifier, linear discriminant analyses, k-nearest neighbor algorithm, support vector machines, and a neural networks based classifier. The pre-built classification model encompassing a predefined set of rules helping predict a skin sample of the individual to be one of a highly attractive or a poorly attractive to mosquitoes, wherein the classification model is pre-built using a set of novel engineered features, wherein the set of novel engineered features is generated using normalized and scaled abundance values corresponding to a plurality of unique taxonomic groups, wherein the set of abundance values is generated via biological samples obtained from a cohort comprising of individuals known to higher or lower degree of mosquito attractiveness. In other words, the binary classifier utilizes the pre-built classification model encompassing a predefined set of rules that help predict a skin sample of the individual to be one of a highly attractive or a poorly attractive to mosquitoes; and wherein the classification model is pre-built using novel engineered features; and wherein the novel engineered features are generated using normalized and scaled abundance values corresponding to a plurality of unique taxonomic groups, and wherein the set of values of the mentioned novel engineered features generated via processing and analysis of biological samples obtained from a cohort comprising of individuals known to have a high degree of attractiveness to mosquitoes are observed to have a statistically significant difference as compared to an analogously obtained set of values obtained from a cohort comprising of individuals known to have a poor or lesser degree of attractiveness to mosquitoes.

In the next step 220, a mosquito attractiveness quotient (MAQ) score is computed by feeding the CFT to the binary classifier using the MAQ score calculation module 120. At step 222, the computed MAQ score is compared with a predefined threshold score, to categorize the individual to be one of a highly attractive or a poorly attractive to mosquitoes using the mosquito attractiveness prediction module 122. The predefined threshold score is a value obtained as an output of the binary classifier and the corresponding prebuilt classification model.

And finally, at step 224, skin microbe based therapeutic interventions is administered to the individual via the administration module 112, if the individual is categorized as highly attractive to mosquitoes. The therapeutic interventions are configured to: combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

The skin bacteria based pre-/pro-/anti-/anti-/meta-/post-/synbiotics or bioengineered beneficial bacteria may be administered in the form of one (or a combination) of routes/mechanisms/administration modes, such as, transdermal skin-patches, woven or non-woven transdermal fabric, anti-bacterial textiles, detergents, lotions, oils, ointments, or sprays that repel mosquitoes by maintaining/promoting the growth of healthy skin microbes. Microbe-based mosquito traps/screens/nets can be fabricated to control mosquito population and/or eradicate their breeding sites. Additionally, bacteriophage and clustered regularly interspaced short palindromic repeats (CRISPR) mediated technology can be utilized to curb the growth of bacterial groups that are responsible for high attractiveness of an individual's skin towards mosquitoes.

According to an embodiment of the disclosure, the system 100 can also be explained with the help of various examples.

Figure 3A:
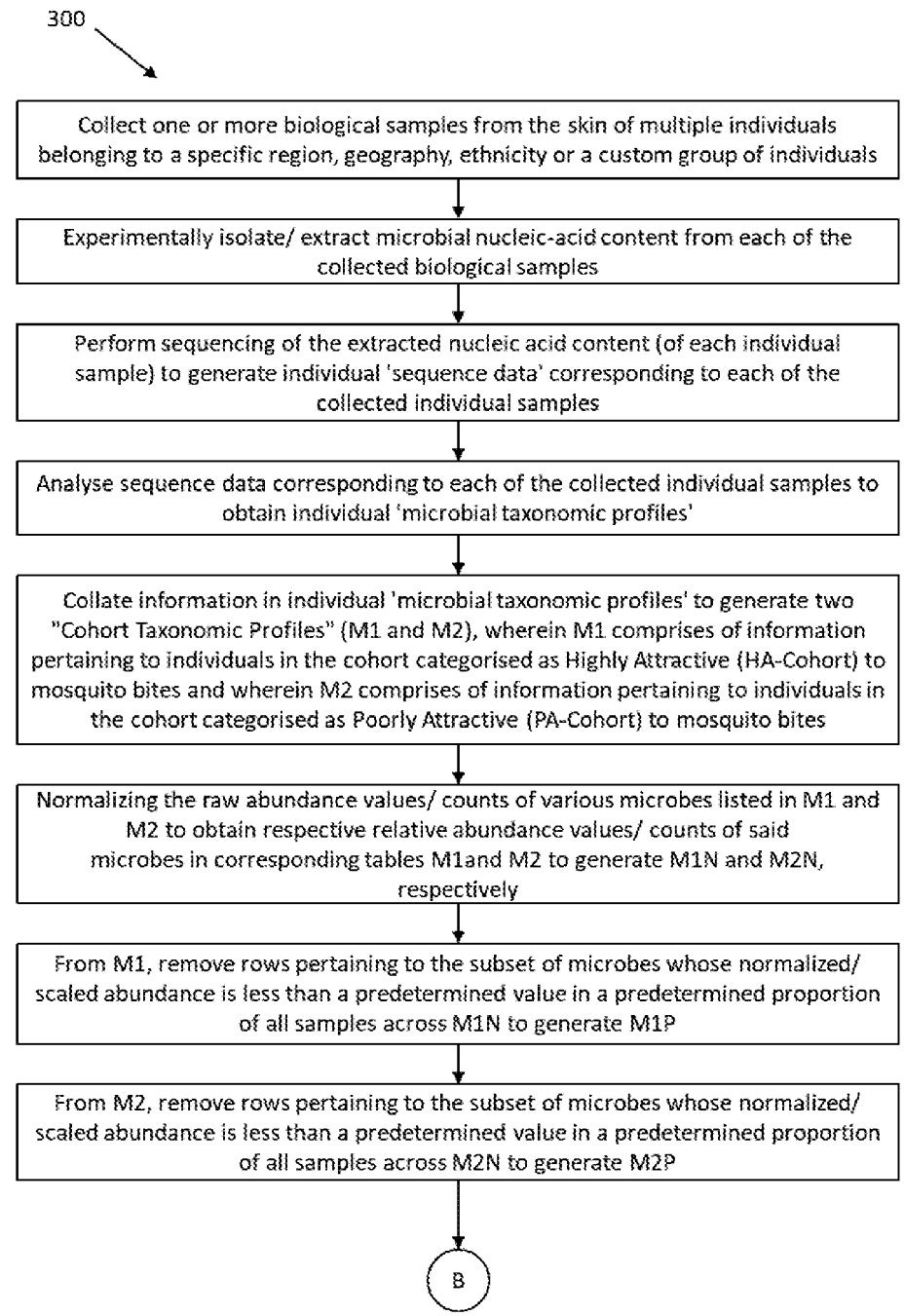
FIGS. 3A and 3B is a flowchart illustrating schematic representation of the methodology used for evaluating and reducing the degree of mosquito-attractiveness of the individual using empirical data investigation according to some embodiments of the present disclosure.
Figure 3B:
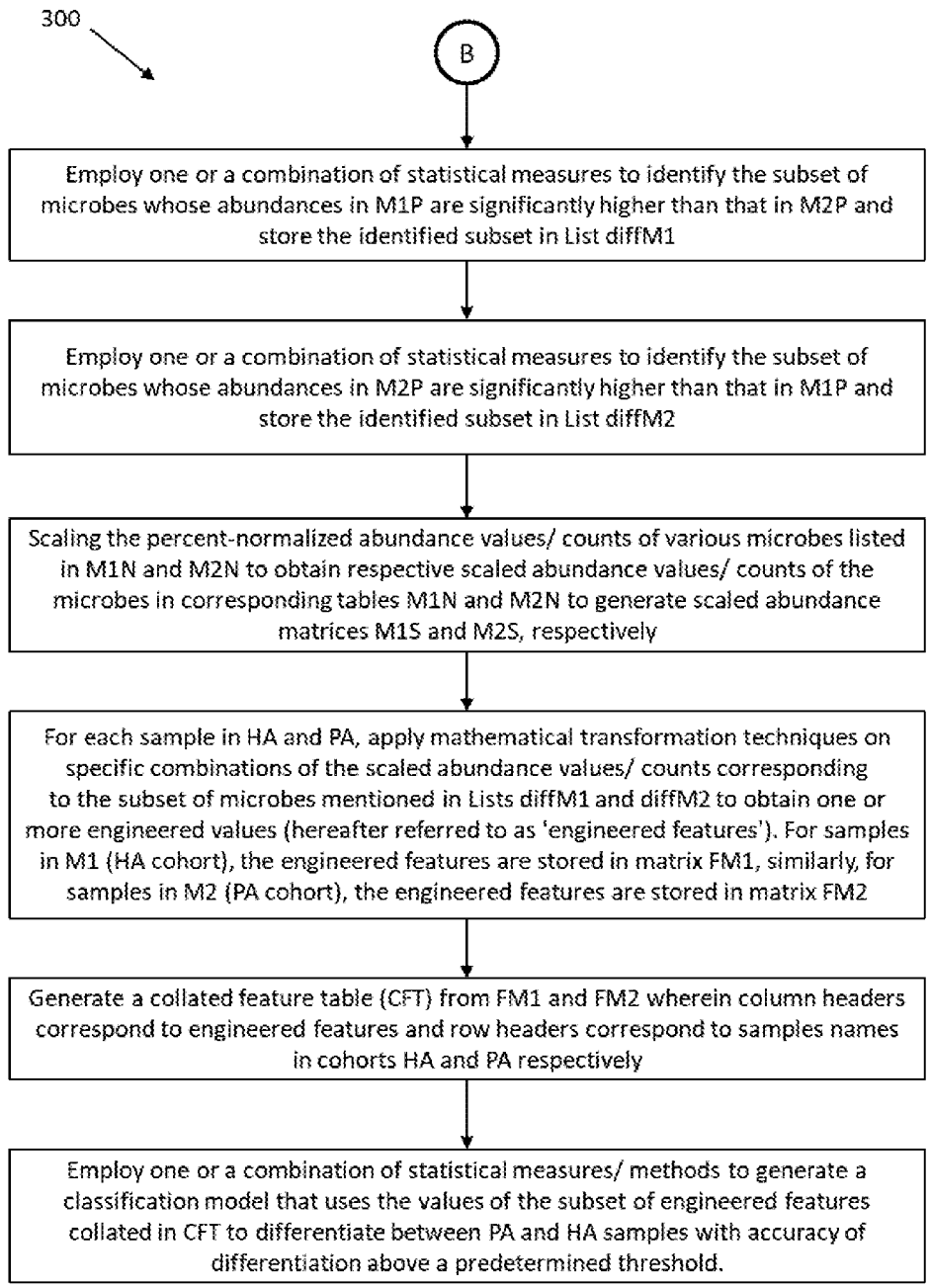

A flowchart 300 illustrating schematic representation of the methodology used for evaluating and reducing the degree of mosquito-attractiveness of the individual using empirical data investigation is shown in FIG. 3A-3B. In an example, for detailed understanding of various methods/steps employed for obtaining a microbial taxonomic profile of a skin sample, publicly available microbial 16S rRNA amplicon sequence data pertaining to skin samples generated in following published study have been utilized: "Composition of Human Skin Microbiota Affects Attractiveness to Malaria Mosquitoes" by Verhulst et al., 2011, with PMCID: PMC3247224. In the mentioned study, skin samples from healthy male volunteers were collected and 16S rRNA sequencing of the microbial nucleic acid content of these samples was performed with objective of evaluating the skin microbiota with respect to the attractiveness/susceptibility of the individual (from whom the respective samples were obtained) towards malaria mosquito bites. As part of the experiments, skin emanations from feet of volunteers were collected by rubbing glass beads to the feet of individual volunteers. Beads with skin emanations from volunteers were assessed for attractiveness to female *Anopheles gambiae* mosquitoes (vectors for malarial parasite *Plasmodium*) through olfactometer bio-assay analysis. A Generalized Linear model (GLM) was used to examine the differences in the relative attractiveness to malarial mosquitoes based on the proportion of mosquitoes caught in olfactometer trapping device containing beads releasing skin emanation of volunteers. The GLM was followed by t-test to identify volunteers with skin odor highly attractive to mosquitoes. The identified subset of volunteers was designated as highly-attractive (HA) cohort. The remaining volunteers found to have feet skin odor that was less attractive to *Anopheles* mosquitoes were assigned into another group, namely, poorly-attractive (PA) cohort. Table 1 provides the details for skin-microbiome samples corresponding to HA and PA cohort in the above mentioned study.

TABLE 1

Details corresponding to 16S rRNA skin microbiome samples from two distinct groups, HA and PA, collected from healthy male volunteers from a pre-existing study.

| Cohort | No. of samples | Body site |
| --- | --- | --- |
| Highly-attractive (HA) | 21 | Foot Skin |
| Poorly-attractive (PA) | 10 | Foot Skin |

Further, the 16S rRNA sequence data corresponding to the above-mentioned skin samples are provided as input to Divisive Amplicon Denoising Algorithm2 (DADA2) version 1.10.0. The DADA2 pipeline classifies the raw 16S rRNA sequence data corresponding to a given sample into 'Amplicon Sequence Variants (ASVs)'. To estimate the abundance of various bacterial taxonomic groups present in the skin sample, the generated ASVs are subsequently compared/matched to sequences in the bacterial 16s rRNA 'Greengenes version 13.8' database. It may be noted that ASVs are unique microbial nucleic acid sequences which differ by as little as a single nucleotide. Detection of ASVs from high-throughput marker gene analysis data provides better resolution in identification of taxonomic composition of the samples. Other methods such as, Naïve Bayesian classifier as implemented in Ribosomal Data Project, that classify microbial sequence reads into taxonomic groups, or methods utilizing sequence based matches with different marker gene databases, such as, Silva, Ribosomal Database Project database can also be applied for analyzing sequence data and estimating the raw counts or abundances of various microbial species/taxonomic groups/taxonomic units in the collected skin sample. The disclosure also supports the creation of an in-house 16S rRNA database of strains of bacterial genomes for customized analysis. Any other method for identifying the microbial composition of a given sample can also be utilized.

The abundances of ASVs obtained in form of raw counts are stored in form of simple mathematical data matrix, referred henceforth as ASV abundance matrix. For samples from HA cohort, the ASV abundance matrix is represented by M1. Similarly, for samples from PA cohort, the ASV abundance matrix is denoted by M2. In both the matrices, individual ASVs are represented as row headers and samples corresponding to skin microbiome of individuals are depicted as column headers. Values in individual cells in the matrices represent the raw abundance counts for respective ASVs in the corresponding input samples. Table 2 shows a subset of the raw abundance at ASV level corresponding to an HA and a PA sample from M1 and M2, respectively.

TABLE 2

Subset of raw ASV abundance values corresponding to an HA and a PA sample from two populations under study.

| ASVs | HA_1 | PA_1 |
|---|---|---|
| ASV_1 | 596 | 92 |
| ASV_2 | 115 | 278 |
| ASV_3 | 103 | 16 |
| ASV_4 | 0 | 345 |
| ASV_5 | 33 | 53 |
| ASV_6 | 44 | 149 |

Normalization of taxonomic abundance profiles: Once the microbiome composition (in form of ASV abundance matrices) of skin samples from two distinct cohorts (HA and PA) is obtained, the matrices, M1 and M2 are provided as input to a hardware processor with software instructions to count-normalize the raw counts/abundances of ASVs into relative abundance values. The count-normalization adjusts the raw abundance values of individual ASVs in each of the samples so that values of individual ASV's across samples are suitably adapted to a common scale, thereby aiding in correcting unintended biases in the estimation of microbial abundances, wherein the said biases may arise due to variation in sampling techniques, library sizes and other technical discrepancies. In the present disclosure, the raw counts of each ASV in matrices M1 and M2 are transformed into percent-normalized proportions that are obtained by dividing the raw ASV counts in a sample by total number of ASV abundance counts in the corresponding sample. The percent-normalized matrices obtained by count-normalizing values of various ASVs in matrices M1 and M2 are denoted by M1N and M2N, respectively.

Percent-normalized ASV abundance matrix for M1=M1N
Percent-normalized ASV abundance matrix for M2=M2N In M1N and M2N, ASVs are represented as rows and samples corresponding to skin microbiome of volunteers are depicted as columns. The values for each cell in M1N and M2N are percent-normalized proportions for each ASV in the corresponding input samples. Table 3 shows a subset of the percent-normalized abundance at ASV level corresponding to an HA and a PA sample from M1N and M2N, respectively.

TABLE 3

Subset of percent-normalized ASV abundance values corresponding to an HA and a PA sample from two cohorts under study

| ASVs | HA_1 | PA_1 |
|---|---|---|
| ASV_1 | 9.71 | 2.17 |
| ASV_2 | 1.87 | 6.57 |
| ASV_3 | 1.67 | 0.37 |
| ASV_4 | 0 | 8.15 |
| ASV_5 | 0.53 | 1.25 |
| ASV_6 | 0.71 | 3.52 |

It should be noted that the use of any kind of normalization or scaling of bacterial abundance values, including percentage, z-score normalization, cumulative sum scaling, percentile scaling, quantile scaling, Atkinson's log transformation, rarefaction, etc., is within the scope of this disclosure.

In order to select the features that better represent the segregation/classification between the skin microbiome samples of HA and PA cohorts, the percent-normalized abundance matrices, M1N and M2N are utilized. Prior to feature engineering, the abundance matrices M1N and M2N are provided as input into a hardware processor configured with software instructions to scale the proportions of microbial abundance values.

In the present disclosure, MinMax Scalar module from python's scikit-learn library (version 0.22.1) is utilized to scale percent-normalized counts of ASVs from 0 to 1 in each sample.

The scaling on microbial counts is performed through one or more of the other methods, such as, maxAbs scaling, robust scaling, quantile scaling, percentile scaling, cumulative sum scaling or Atkinson's log-ratio transformation is also within the scope of the invention.

Further, log transformation of scaled ASV abundances (for a given input sample) is performed by calculating the logarithm base 10 values of MinMax scaled ASV abundances. To tackle log value error that might arise due to null/zero values in abundance matrices, prior to log transformation, a minuscule numerical value is added to all ASV abundance counts of a sample.

Further, for the purpose of engineering the novel features for each sample, the taxonomic groups/units that are significantly enriched in the two study cohorts (HA and PA) are identified and utilized. The significantly differentiating ASVs associated with abundance matrices M1 (for HA cohort) and M2 (for PA cohort) are stored in lists 'diffM1' and 'diffM2', respectively. Further, for each sample novel features in one embodiment are designed by calculating the ratio or quotient of log transformed scaled abundances of all ASVs in 'diffM1' to log transformed scaled abundances of all ASVs in 'diffM2', that is described by the following equation:

$$F_{ij} = \log(\text{diff}M1)/\log(\text{diff}M2)$$

where F represents the novel engineered feature obtained by dividing log transformed scaled values of each ASV "i" that is differentially abundant in M1 (listed in 'diffM1') with the log transformed scaled values of each ASV "j" that is differentially abundant in M2 (listed in 'diffM2'). For a skin microbiome sample, a higher value of a feature Fij would indicate a greater risk of being bitten by mosquito bites as opposed to a lower value of feature Fij. A total of 12 features are designed. Table 4 below contains the values of engineered features for a subset of test samples from M1 and M2.

TABLE 4

Table showing engineered features for a subset of test samples

| Features | Test Sample 1 | Test Sample 2 |
|---|---|---|
| Feature 1 | 0.14 | −2.04 |
| Feature 2 | 0.53 | −2.6 |
| Feature 3 | 0.49 | −2 |
| Feature 4 | 1.01 | −0.76 |

It should be noted that any state-of-art feature engineering methodologies, such as, mathematical transformations, grouping operations, data or feature splitting, data binning, etc. are well within the scope of this disclosure to extract meaningful features from raw/normalized/scaled/transformed microbial abundance data.

The values of the engineered features are provided as an input to a pre-computed binary classification model that identifies putative biomarkers segregating the two distinct cohorts under study. For the purpose of model generation, 'Weighted Logistic regression' (WLR) classifier (from python's linear-model module of scikit-learn package version 0.22.1) is utilized. WLR is a predictive analysis algorithm based on the concept of probability. Mathematically, it outputs the probability values of individual samples predicted to be present in either of the two categories used in classification (PA & HA, in this case). For each sample (provided as an input to the classifier), the WLR model generates a probability/likelihood for the sample to be classified into either highly-attractive class or into poorly-attractive class. Thus, for a given microbiome sample obtained from the skin of an individual, the Mosquito Attractiveness Quotient (MAQ) is defined as predicted probability value obtained through the constructed WLR model.

Following methodology have been used for feature engineering and model generation using empirical data investigation. By utilizing the results of olfactometer bioassay analysis on skin emanations of healthy male volunteers, the volunteers were grouped into two cohorts, viz., highly-attractive (HA) and poorly-attractive (PA) to mosquito bites as explained earlier.

The feature engineering and model computation comprises of the following steps:
1. Pre-processing of microbial abundance data: For removing sparsity and inconsistencies in microbial count/abundance data, the percent-normalized abundance matrices M1N and M2N are pre-processed and de-noised. In this step, the rows corresponding to the ASVs having missing/null abundance values in at–least 90% of the samples (represented as columns) of either percent-normalized abundance matrix M1N or M2N are removed. The corresponding pre-processed abundance matrices obtained by removal of sparse ASVs from M1N and M2N are denoted by M1P and M2P, respectively.

Pre-processed ASV abundance matrix for M1N=M1P
Pre-processed ASV abundance matrix for M2N=M2P In both M1P and M2P, ASVs having non-zero abundance values in at-least 90% of the samples corresponding to M1N and M2N, respectively, are represented as rows headers and skin microbiome samples are depicted as columns headers. The values for each cell in M1P and M2P are percent-normalized proportions for each of the filtered ASVs in the corresponding samples.

2. Identification of differentially abundant taxonomic groups/units: After pre-processing, the matrices, M1P and M2P, are fed into a hardware processor with software instructions to compare the abundances of bacterial groups between the two cohorts (HA and PA). These comparisons can be performed through univariate or multivariate parametric or non-parametric statistical tests. This step is imperative in identifying the subset of microbes showing a statistically significant difference in their abundance/proportions between each of studied cohorts. Any of the standardized statistical methods or models for comparison of microbiome data, such as, standard t-test, non-parametric Wilcoxon rank-sum test, analysis of variance, Kruskal-Wallis test, chi-square test, or machine learning based algorithms including decision trees, neural networks, random forests, etc., are within the scope of the disclosure.

In another implementation, a single skin sample can be collected from an individual, and the abundances of bacteria in the sample can be compared against a reference or pre-determined threshold values for the corresponding bacteria in a different sample obtained from the same individual at different time-point(s). In the present disclosure, in one implementation, ASVs (corresponding to distinct bacterial groups) having significantly different abundances between the two analyzed groups are identified using Lefse tool with an LDA cut-off of >=2, at a p-value of 0.05. Further, 'significantly differentiating' ASVs (i.e. ASVs having a statistically significant difference in their abundance/proportions between the two groups viz., HA and PA) having non-zero abundance values in at least 50% of the samples of M1P and M2P are stored in lists 'diffASVM1' and 'diffASVM2', respectively. The processor is then configured to map/taxonomically classify/assign the nucleotide sequences of ASVs stored in 'diffASVM1' and 'diffASVM2' to the closest bacterial groups at specie or strain level, by utilizing homology based search of sequences of ASVs against sequences in reference databases.

3. Feature extraction and engineering: Further, the abundance values of the significantly differentiating ASVs between the two cohorts (HA and PA), stored in lists 'diffASVM1' and 'diffASVM2', are employed to design novel features that better represent the segregation or classification between the skin microbiome samples of HA and PA cohorts. To achieve this, the percent-normalized abundance matrices, M1N and M2N are provided as input into a hardware processor configured with software instructions to scale the proportions of microbial abundance values. This 'scaling' step comprises of transforming the microbial abundance values in each sample to represent the abundance in form of scaled values, wherein the scaling on microbial counts is performed through one or more of the methods, such as, MinMax scaling, MaxAbs scaling, robust scaling, quantile scaling, percentile scaling, cumulative sum scaling or Atkinson's log-ratio transformation. For instance, MinMax scaling is performed using the following equation:

$$X = X - \frac{X_{min}}{X_{max}} - X_{min}$$

where, X represents the percent-normalized abundance count of ASV, $X_{min}$ represents the minimum percent-normalized abundance value of all ASVs in the corresponding sample, $X_{max}$ denotes the maximum percent-normalized abundance value of all ASVs in the corresponding sample.

4. In the present disclosure, MinMax Scalar module from python's scikit-learn library (version 0.22.1) is utilized to scale percent-normalized counts of ASVs from 0 to 1 in each sample. The corresponding scaled matrices obtained by transforming the percent-normalized matrices M1N and M2N are denoted by M1S and M2S, respectively.

MinMax Scaled ASV abundance matrix for M1N=M1S
MinMax Scaled ASV abundance matrix for M2N=M2S Table 5 shows a subset of the MinMax scaled abundances at ASV level corresponding to an HA and a PA sample from M1S and M2S, respectively.

TABLE 5

Subset of MinMax scaled ASV abundance values corresponding to an HA and a PA sample from two populations under study.

| ASVs | HA_1 | PA_1 |
|---|---|---|
| ASV_1 | 0.63 | 0.26 |
| ASV_2 | 0.12 | 0.8 |
| ASV_3 | 0.11 | 0.04 |
| ASV_4 | 0 | 1 |
| ASV_5 | 0.03 | 0.15 |
| ASV_6 | 0.04 | 0.43 |

Log transformation of matrices M1S and M2S is subsequently performed by calculating the logarithm base 10 values of MinMax scaled ASV abundances. In order to tackle log value error that might arise due to null values in matrices, prior to log transformation, a minuscule numerical value is added to all abundance values. For every sample in M1S and M2S, the log transformed scaled abundance values of ASVs from list 'diffASVM1' are extracted and stored in matrix 'diffM1'. Similarly, for every sample in M1S and M2S, the log transformed scaled abundance values of ASVs from list 'diffASVM2' are extracted and stored in matrix 'diffM2'.

Further, for each sample in M1S and M2S, novel features are designed by calculating the ratio or quotient of log transformed scaled abundances of all ASVs in 'diffM1' to log transformed scaled abundances of all ASVs in 'diffM2' that is described by the following equation as explained above:

$$F_{ij} = \log(\text{diff}M1)/\log(\text{diff}M2)$$

where F represents the novel engineered feature obtained by dividing log transformed scaled values of each ASV "i" that is differentially abundant in M1N (listed in 'diffASVM1') with the log transformed scaled values of each ASV "j" that is differentially abundant in M2N (listed in 'diffASVM2'). A total of 12 features are designed. The novel engineered matrices, for M1N and M2N are denoted by FM1 and FM2 respectively.

Engineered feature abundance matrix for M1=FM1
Engineered feature abundance matrix for M2=FM2

The rows in matrices FM1 and FM2, represent individual samples in M1 and M2 and the columns contain the novel engineered features. Each cell of the matrices FM1 and FM2 contains computed values of engineered features corresponding to a particular sample. For a skin microbiome sample, a higher value of a feature Fij would indicate a greater risk of being bitten by mosquito bites as opposed to a lower value of feature Fij. It should be noted that any state-of-art feature engineering methodologies, such as, mathematical transformations, grouping operations, data or feature splitting, data binning, etc. can be adopted to extract meaningful features from raw/normalized/scaled/transformed microbial abundance data. Further, the feature matrices FM1 and FM2 are concatenated/joined to generate a Collated Feature Table (CFT) that encompasses the engineered features for all the samples from HA and PA cohort. The column headers of CFT represent the engineered features and the row headers correspond to sample names of HA and PA cohort respectively. Each cell of CFT corresponding to a sample contains the values of engineered features for the respective sample. Table 6 below represents a prototype of CFT containing a subset of engineered features for an HA sample and a PA sample.

TABLE 6

Subset of Collated Feature Table (CFT) showing features engineered for an HA and a PA sample.

| Samples | Feature 1 | Feature 2 | Feature 3 | Feature 4 |
|---|---|---|---|---|
| HA_1 | 1.64 | 0.21 | 0.1 | 0.22 |
| PA_1 | 0.95 | −0.05 | −0.01 | −0.02 |

5. Generation of classification model: The values of the engineered features are fed into a processor configured with software instructions to generate a binary classification model to identify putative biomarkers that segregates the two experimental cohorts under study. For this purpose, 'Weighted Logistic regression' (WLR) classifier (from python's linear-model module of scikit-learn package version 0.22.1) is utilized. Weighted logistic regression is a classification technique that penalizes mistakes during model fit by telling the model to pay more attention to the minority class. This kind of penalization effectively addresses the challenges of class prediction in slightly skewed or highly imbalanced datasets. The novel engineered features in CFT are used as features for training the WLR classifier. The sample set of the two cohorts (21 HA samples and 10 PA samples) present in CFT are randomly divided into training and test set samples, in a ratio of 70:30 (70% of the samples as training set and the remaining 30% as the test set). Stratified random sampling is utilized to select random samples for train and test sets. This ensures that each class under study is properly represented in both train and test sets. Before training the model, top features are selected using scikit-learn feature selection module (version 0.22.1). WLR model is built using the train set with stratified cross-fold validations (5-fold, repeated 100 times). To mitigate the risk of over-fitting while training the model and to increase the model's interpretation, penalized L2-regularization (with a C penalty of 0.1) is applied during model generation. After training and repeated cross-validation, the final model is validated using the test set. Further, the performance of the model obtained is evaluated through values of accuracy, 'area under curve' (AUC) of the 'receiver operating characteristics' (ROC), precision, recall and F-measure of the model obtained from python's metrics module of scikit-learn package (version 0.22.1). It is should be noted that any of the standardized machine learning algorithms, similar to but not limited to, random forest, decision trees techniques, naive Bayes, linear discriminant analyses, k-nearest neighbor algorithm, Support Vector Machines, Neural Networks, etc. may be utilized for binary classification.

6. Defining prediction rules and threshold: Logistic regression is a predictive analysis algorithm based on the concept of probability. Mathematically, it outputs the probability values of individual samples predicted to be present in either class 0 or 1 (PA & HA, in this case). For each sample, at threshold probability value of 0.5, the probability values equal to or greater than the threshold are assigned to class 1 (HA) and values less than the threshold are assigned to class 0 (PA). Thus, for a given microbiome sample obtained from the skin of an individual, the mosquito attractiveness quotient (MAQ) is defined as predicted probability value obtained through the constructed WLR model. The risk of an individual to mosquito bites can be predicted based upon the following rules derived from WLR model.

MAQ>0.5 indicates significant risk of mosquito bites.
MAQ<=0.5 indicates low or no risk of mosquito bites.

Many physiological factors specific to the host, such as, age, gender, skin pH, temperature, humidity, oxygen and nutrient availability, sebum and hormone secretion, immune system, etc., are also responsible for the variability of skin flora. In addition, geographic and ethnic differences majorly contribute towards inter-individual fluctuations in skin microbiota. Therefore, any kind of feature engineering from raw abundances of skin bacteria or any method to estimate skin microbiota's taxonomic or functional repertoires that alone, or in any combination, measure the likelihood of mosquito-attractiveness of a given sample, may prove to be an efficient assessment/screening method for individuals from a different geography or/and of different ethnicity/lifestyle.

Following methodology have been used for performance evaluation of the computed classification model and for threshold generation for risk assessment of attractiveness/susceptibility to mosquito bites.

In order to train and validate the model, the feature matrix (CFT) was randomly split into training and test set samples in a ratio of 70:30 (70% of the samples were randomly chosen as training set and the remaining 30% as the test set). After training and validations, the performance of the model obtained is evaluated through accuracy, 'area under curve' (AUC), precision, recall and F-measure values obtained from python's metrics module of scikit-learn package (version 0.22.1). The parameters showing the model efficiencies for training and test sets, averaged over 100 repetitions are provided below in Table 7.

TABLE 7

Parameters depicting the model's performance and classification efficiencies.

| Classifier | Train accuracy | Train AUC | Test accuracy | Test AUC | Precision | Recall | F-measure |
|---|---|---|---|---|---|---|---|
| WLR | 0.84 | 0.89 | 0.8 | 0.86 | 1 | 0.71 | 0.83 |

It should be noted that the WLR classifier used in the current implementation of the disclosure, predicts mathematical probabilities of samples to be classified into either of the two experimental classes or groups (highly-attractive or poorly-attractive cohorts, in this case). In case of binary classification, the WLR model selects a probability threshold of 0.5 which mathematically indicates the possibility of a sample to belong to either of the two classes. In view of this, for each sample (present in both training and test data) used in classification, the probabilities of class memberships are predicted by the fitted and validated WLR model. Table 8 shown below provides the percentage of samples from the two study groups and their predicted class membership based upon the output probabilities of WLR model.

TABLE 8

The proportion of samples from two studied cohorts and their predicted class membership obtained through WLR.

| Proportion of samples | Class Membership | |
|---|---|---|
| (%) | HA | PA |
| HA | 86 | 14 |
| PA | 10 | 90 |

It is also observed that model generation and validation using raw bacterial abundance/count data strikingly reduces the model's efficiency and performance. Hence, engineering meaningful features amplify the microbiome signals of a given sample and consequently result in improved classification. Table 9 shows the model performance parameters using raw bacterial counts/abundances.

TABLE 9

Parameters showing model efficiency and classification parameters based on raw ASV abundance profiles.

| Classifier | Train accuracy | Train AUC | Test accuracy | Test AUC | Precision | Recall | F-measure |
|---|---|---|---|---|---|---|---|
| WLR | 0.8 | 0.7 | 0.7 | 0.59 | 0.75 | 0.85 | 0.8 |

Mathematically in an example, the threshold probability value of 0.5 is assigned for risk assessment as described in the later part of the disclosure. The risk for attractiveness/susceptibility to mosquito bites is ascertained through the rules described below—

MosAQuo>0.5 indicates significant risk of mosquito bites.
MosAQuo<=0.5 indicates low or no risk of mosquito bites.

By computing probability value of MAQ and comparing the same with the pre-defined threshold, via one or more software processors, any new skin microbiome sample can be predicted to be either highly-attractive or poorly-attractive to mosquitos. Thus, the risk of a person to mosquito bites can thus be assessed through the composition of their skin microbes.

Further, following methodology has been used for formulation of microbe-based screening/preventive/therapeutic interventions to effectively reduce and manage the mosquito-attractiveness of the individual. For the formulation of these microbiome-based vector-management approaches, it is imperative to identify specific bacterial groups that either produce attractive volatile organic compounds (VOCs) or inhibit the release of VOCs. In this view, the skin microbiome samples from individuals having skin odor experimentally characterized to be highly-/poorly-attractive to mosquitoes are investigated. In the present disclosure, the bacterial groups that are significantly enriched in the skin-microbiome data of either HA or PA group are identified. The Amplicon Sequence Variants (ASVs) (corresponding to distinct bacterial groups) having significantly different abundances between the two analyzed groups (HA and PA) are predicted using Lefse tool, with an LDA cut-off of >=2, at a p-value of 0.05. Further, significant differential ASVs having non-zero abundance values in at least 50% of the samples of both highly-attractive and poorly-attractive cohorts are stored in lists 'diffM1' and 'diffM2', respectively. The taxonomic abundance profiles/matrices for HA samples and PA samples are denoted by M1 and M2 as explained earlier. Hence, for the purpose of consistency in notations, the lists for differential taxonomic groups/units enriched in HA and PA samples are denoted as 'diffM1' and 'diffM2', respectively. It may be noted that any of the standardized statistical methods or models for comparison of microbiome data, such as, standard t-test, non-parametric Wilcoxon rank-sum test, analysis of variance, Kruskal-Wallis test, chi-square test, or machine learning based algorithms including decision trees, neural networks, random forests, etc., are well within the scope of this disclosure. In some other methods, a single sample can be collected from an individual, and the abundances of bacteria in the sample can be compared against a reference or threshold values for the corresponding bacteria in a different sample obtained from the same individual at different time-point(s). It should be appreciated that many physiological factors specific to the host, such as, age, gender, skin pH, temperature, humidity, oxygen and nutrient availability, sebum and hormone secretion, immune system, etc., are responsible for the variability of skin flora. In addition, geographic and ethnic differences majorly contribute towards inter-individual fluctuations in skin microbiota. Therefore, in alternative implementations, for samples collected from a different geography or from volunteers from another ethnicity, the taxonomic groups/units identified and listed in 'diffM1' and 'diffM2' may vary according to the structure and composition of the resident skin bacteria showing prevalence/presence in individuals from the said geography/ethnicity.

Further, nucleotide sequences of ASVs stored in 'diffM1' and 'diffM2' are mapped to the closest bacterial groups at specie or strain level, by utilizing sequence homology based search against reference genome databases. The nucleotide sequences (of differentially abundant ASVs) are queried using BLAST tool against an array of reference databases, such as, bacterial marker gene databases, reference RNA databases, and representative genome databases, etc. It should be noted that any other method for querying nucleotide or protein sequences, which may include but are not limited to gene homology, Hidden Markov Model based identification (Protein Family or PFAM Database etc.), Position Specific Scoring matrices (PSSM), motif search etc., are within the scope of this disclosure. Table 10 shown below lists ASVs in 'diffM1', along with their sequences and the corresponding closest organism mapped through BLAST.

TABLE 10

List of significantly increased ASVs in skin samples of HA group (diffM1), along with their nucleotide sequences and closest organism mapped through BLAST.

| | Nucleotide Sequence | BLAST hit at strain level (Threshold of >=99% sequence identity, 100% coverage and e-value <= 1e-5) |
|---|---|---|
| ASV_1 | CTGGACCGTGTCTCAGTTCCAG TGTGGCCGATCACCCTCTCAG GTCGGCTACGCATCGTTGCCTT GGTAAGCCGTTACCTTACCAAC TAGCTAATGCGGCGCGGATCC ATCTATAAGTGACAGCAAGACC GTCTTTCACTGTTGAACCATGC GGTTCAACATGTTATCCGGTAT TAGCTCCGG TTCCCGAAGTTATCCC | Staphylococcus caprae strain DSM 20608 Staphylococcus capitis strain ATCC 27840 Staphylococcus capitis strain JCM 2420 Staphylococcus caprae strain ATCC 35538 Staphylococcus capitis subsp. urealyticus strain MAW 8436 Staphylococcus capitis strain LK 499 |
| ASV_2 | CTGGGCCGTATCTCAGTCCCAA TGTGGCCGTCCACCCTCTCAGG CCGGCTACCCGTCGCCGCCTTG GTAGGCCATTACCCCACCAACA AGCTGATAGGCCGCGAGCTCAT CCTACACCGAAAAAACTTTCAA CCATCACACTAAAAATGGTTCCT ATCGGTATTAGACCCAGTTTCC CAGGCTTATCCCGAAGTGCAG | Corynebacterium tuberculostearicum strain Medalle X, Corynebacterium tuberculostearicum strain ATCC 35692 |

Similarly, Table 11 shown below lists ASVs in 'diffM2', along with their sequences and the corresponding closest organism mapped through BLAST.

TABLE 11

List of significantly increased ASVs in skin samples of PA cohort diffM2), long with their nucleotide sequences and closest organism mapped through BLAST.

| | Nucleotide Sequence | BLAST hit at strain level (Threshold of >=99% sequence identity, 100% coverage and e-value <= 1e-5) |
|---|---|---|
| ASV_3 | CTGGGCCGTGTCTCAGTCCC AGTGTGGCTGGTCGTCCTCT CAGACCAGCTACAGATCGTC GGCTTGGTGAGCCTTTACCT CACCAACTACCTAATCTGATA TCGGCCGCTCCAATCGCGCG AGGTCTTGCGATCCCCCGCT TTCACCCTCAGGTCGTATGC GGTATTAGCTGCTCTTTCGA GCAGTTATCCCCCACGACT | *Pelomonas puraquae* strain Ps10g |
| ASV_4 | TTGGGCCGTGTCTCAGTCCC AATGTGGCTGATCATCCTCT CAGACCAGCTACTGATCGTC GCCTTGGTAGGCCATTACCC TACCAACTAGCTAATCAGAC GCGGGCCGATCTTTCGGCGA TAAATCTTTCCCCGTAAGGG CTTATCCGGTATTAGCACAA GTTTCCCTGTGTTGTTCCGAA CCAAAAGGTACGTTCCCAC | *Bradyrhizobium stylosanthis* strain BR 446<br>*Bradyrhizobium ingae* strain BR 10250<br>*Bradyrhizobium ganzhouense* strain RITF806<br>*Bradyrhizobium centrosematis* strain A9<br>*Bradyrhizobium iriomotense* strain NBRC 102520<br>*Bradyrhizobium denitrificans* strain IFAM 1005<br>*Bradyrhizobium huanghuaihaiense* strain CCBAU 23303 *Bradyrhizobium arachidis* strain CCBAU 051107<br>*Bradyrhizobium iriomotense* strain EK05<br>*Bradyrhizobium denitrificans* strain LMG 8443<br>*Bradyrhizobium guangxiense* strain CCBAU 53363<br>*Bradyrhizobium guangdongense* strain CCBAU 51649 |
| ASV_5 | CTGGGCCGTGTCTCAGTCCC AGTGTGGCTGGTCGTCCTCT CAGACCAGCTACAGATCGTC GGCTTGGTAGGCCTTTACCC CACCAACTACCTAATCTGATA TCGGCCGCTCCAATCGCGCG AGGTCCGAAGATCCCCCGCT TTCACCCTCAGGTCGTATGC GGTATTAGCTGCTCTTTCGA GCAGTTATCCCCCACGACT | *Roseateles aquatilis* strain CCUG 48205 |
| ASV_6 | CTGGGCCGTGTCTCAGTCCC AGTGTGGCTGATCATCCTCTC AGACCAGCTACTGATCGTCG CCTTGGTGAGCCATTACCTCA CCAACTAGCTAATCAGACGCG GGCCGATCTTTCGGCGATAAA TCTTTCCCCGTTAGGGCTTAT CCGGTATTAGCTGAAGTTTCC CTCAGTTGTTCCGAACCAAAA GGTACGTTCCCAC | *Bradyrhizobium elkanii* strain USDA 76 |
| ASV_7 | TTGGACCGTGTCTCAGTTCCA ATGTGGGGGACCTTCCTCTCA GAACCCCTATCCATCGAAGAC TAGGTGGGCCGTTACCCCGC CTACTATCTAATGGAACGCAT CCCCATCGTCTACCGGAATAC CTTTAATCATGTGAACATGTG AACTCATGATGCCATCTTGTA TTAATCTTCCTTTCAGAAGGC TGTCCAAGAGTA | *Bacteroides vulgatus* ATCC 8482<br>*Bacteroides vulgatus* strain JCM 5826<br>*Bacteroides vulgatus* strain JCM 5826 |

TABLE 11-continued

List of significantly increased ASVs in skin samples of PA cohort diffM2), long with their nucleotide sequences and closest organism mapped through BLAST.

| | Nucleotide Sequence | BLAST hit at strain level (Threshold of >=99% sequence identity, 100% coverage and e-value <= 1e-5) |
|---|---|---|
| ASV_8 | CTGGGCCGTGTCTCAGTCCC AGTGTGGCTGGTCGTCCTCTC AGACCAGCTACAGATCGTCG GCTTGGTAGGCCTTTACCCCA CCAACTACCTAATCTGATATC GGCCGCTCCAATCGCGCGAG GTCCGAAGATCCCCCGCTTTC ACCCTCAGGTCGTATGCGGT ATTAGCTGCTCTTTCGAGCAG TTATCCCCCAGACTG | *Roseateles aquatilis* strain CCUG 48205 |

After the Mosquito Attractiveness Quotient (MAQ) evaluation, if an individual is found at a greater risk to mosquito bites (or is identified as highly attractive to mosquitoes), skin microbiome based therapeutic interventions can be designed that combat the growth of bacterial groups listed in 'diffM1'. The growth of bacterial groups (listed in 'diffM1') found to be enriched in skin of individuals identified as highly-attractive to mosquito bites can be curbed by application of transdermal (application on skin) antibiotic patches or formulations, and/or through bacteriophage and CRISPR mediated technologies Further, microbiome based therapeutic interventions in form of pre-/pro-/meta-/post-/synbiotics can be designed that aid colonization of bacterial groups listed in 'diffM2'. The members of the bacterial groups listed in 'diffM2' are experimentally characterized to be producers of an important health-modulating metabolite, butyrate. This short chain fatty acid (SCFA) produced by skin commensals attenuates skin inflammation by stimulating the resident skin T regulatory (Treg) cells. Treg cells constitute a subset of CD4+T cells that primarily maintain skin barrier function by inhibiting/suppressing cutaneous inflammation during the events of skin dysregulation.

In addition, the bacterial groups listed in 'diffM2' biosynthesize the beneficial SCFA propionate and aid in the metabolism of essential vitamins, such as, niacin, biotin, riboflavin, and thiamine. Improper metabolism of the above-mentioned vitamins on skin-barrier enhances the relative degree of attractiveness towards mosquitoes. For instance, faulty oxidation of riboflavin leads to the release of amine trimethylamine in sweat, urine, and breath. Similarly, improper metabolism of biotin on skin enhances the production of branched chain fatty acids, particularly isovaleric acid. Both trimethylamine and isovaleric acid are important mosquito attractant chemicals contributing to the attractive skin odor. Given the role of skin bacterial groups in biosynthesis/metabolism of metabolites that deter/repel the host-seeking mosquitoes, the bacterial strains listed in diffM2 may be provided as pre-/pro-/meta-/post-/synbiotic formulations in order to maintain healthy skin microbiome. Further, chemical-free, safe and effective mosquito repellents can be designed that either inhibit the colonization of bacteria listed in Table 10, or block the release of volatile attractive metabolites produced by them. Such metabolites, include, ammonia and a range of branched-chain organic acids, thiols and aldehydes that are produced by the action of skin bacteria on components of human sweat. The skin-bacteria based pre-/pro-/anti-/meta-/post-/synbiotics may be administered in the form of any one (or a combination) of routes, such as, transdermal skin-patches, woven and non-woven transdermal fabric, anti-bacterial textiles, detergents, lotions, oils, ointments, sprays that repel mosquitoes by maintaining the consortium of healthy skin microbes. Microbe-based mosquito traps/screens/nets can be fabricated to control mosquito population and eradicate the breeding sites.

It may also be noted that the risk-assessment method proposed in the present disclosure can be incorporated into routine health screening protocols as a simple, cost-effective and non-invasive/minimally-invasive (using skin samples) solution to measure/evaluate the risk/susceptibility of an individual to mosquito bites. Such screening protocols can widely facilitate the applicability of early and effective preventive/therapeutic regimens, especially in scenarios wherein an individual plans to travel to geographic areas/locations/countries with high abundance of disease carrying mosquito population.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The disclosure herein addresses unresolved problem related to design and deployment of microbiome-based personalized vector management approaches reducing mosquito attractiveness in an individual. The embodiment thus provides the method and system for evaluating and reducing the degree of mosquito-attractiveness of an individual.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g.

an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs, GPUs etc.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for evaluating and reducing the degree of mosquito-attractiveness of an individual, the method comprising:
   collecting a biological sample from skin of the individual, wherein the biological sample is representing skin microbiome of the individual;
   extracting, via an extraction unit, microbial nucleic acid content from the collected biological sample;
   sequencing the extracted microbial nucleic acid content, via a sequencer, to get sequence data;
   categorizing, via one or more hardware processors, the sequenced data into a plurality of taxonomic groups utilizing standardized classification algorithms and a plurality of databases;
   computing, via the one or more hardware processors, raw abundance values of a plurality of features, wherein each feature corresponds to a unique taxonomic group from amongst the plurality of taxonomic groups;
   normalizing and scaling, via the one or more hardware processors, the computed raw abundance values of each of the plurality of features, wherein the normalizing is configured to adjust the raw abundance values to a common scale, thereby correcting a bias in the computation of the raw abundance values, wherein the bias is due to a plurality of factors;
   identifying, via the one or more hardware processors, a set of features amongst the plurality of features based on similarity between a nucleotide sequence corresponding to the feature and the nucleotide sequences corresponding to a set of pre-identified amplicon sequence variants (ASVs), and wherein the set of features is identified if the similarity exceeds a pre-defined range;
   performing, via the one or more hardware processors, one or more feature engineering techniques on the normalized and scaled abundance values of the set of features to obtain a collated feature table (CFT), wherein the CFT comprises of a plurality of novel engineered features and their corresponding engineered abundance values;
   providing, via the one or more hardware processors, a binary classifier, wherein the binary classifier utilizing a pre-built classification model;

computing, via the one or more hardware processors, a mosquito attractiveness quotient (MAQ) score by feeding the CFT to the binary classifier;

comparing, via the one or more hardware processors, the computed MAQ score with a predefined threshold score, to categorize the individual to be one of a highly attractive or a poorly attractive to mosquitoes; and administering, via an administration module, skin microbe based therapeutic interventions to the individual, if the individual is categorized as highly attractive to mosquitoes, wherein the therapeutic interventions are configured to:

combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

2. The processor implemented method of claim 1 further comprises fabricating microbe-based mosquito traps to control mosquito population and eradicate mosquito breeding sites.

3. The processor implemented method of claim 1, the therapeutic interventions are administered in the form of one or a combination of skin bacteria based transdermal skin-patches, woven and non-woven transdermal fabric, antibacterial textiles, lotions, oils, ointments, mosquito repelling sprays, bacteriophage and clustered regularly interspaced short palindromic repeats (CRISPR) mediated technology to curb the growth of bacterial groups bio-synthesizing compounds responsible for high attractiveness of the individual's skin towards mosquitoes.

4. The processor implemented method of claim 1, wherein the sample is collected from a one or more body sites further comprising arms, feet, palms, ankles, back of neck, knees, elbows, or face.

5. The processor implemented method of claim 1, wherein the pre-built classification model encompassing a predefined set of rules helping predict a skin sample of the individual to be one of a highly attractive or a poorly attractive to mosquitoes, wherein the classification model is pre-built using a set of engineered features, wherein the set of novel engineered features is generated using normalized and scaled abundance values corresponding to a plurality of unique taxonomic groups, wherein the set of abundance values is generated via biological samples obtained from a cohort further comprising of individuals known to higher or lower degree of mosquito attractiveness.

6. The processor implemented method of claim 5, wherein the plurality of unique taxonomic groups are microbial groups present in skin of individuals who are either highly-attractive to mosquitoes or poorly-attractive to mosquitoes.

7. The processor implemented method of claim 1, wherein the predefined threshold score is a value obtained as an output of the binary classifier and the corresponding prebuilt classification model.

8. The processor implemented method of claim 1, wherein the one or more feature engineering techniques the comprise of applying mathematical transformation on a predefined combinations of the normalized and scaled abundance values corresponding to an identified set of features to obtain novel features and corresponding engineered abundance values.

9. The processor implemented method of claim 1, wherein the predefined range is between 80-100 percent sequence identity value.

10. The processor implemented method of claim 1, wherein quantification of similarity is done using one of a plurality of techniques further comprising a homology search, a BLAST searching, a Hidden Markov Model based search, a Position Specific Scoring matrices (PSSM), and a motif search.

11. The processor implemented method of claim 1, wherein the binary classifier is one of a Weighted Logistic regression' (WLR) classifier, a random forest classifier, a decision trees technique, a naive Bayes classifier, linear discriminant analyses, a k-nearest neighbor technique, a support vector machines, and a neural networks based classifier.

12. The processor implemented method of claim 1, wherein the plurality of factors comprises variation in sampling techniques, library sizes and technical discrepancies during the extracting and sequencing steps.

13. A system for evaluating and reducing the degree of mosquito-attractiveness of an individual, the system comprises:

a sample collection module for collecting a biological sample from skin of the individual, wherein the biological sample is representing skin microbiome of the individual;

an extraction unit for extracting microbial nucleic acid content from the collected biological sample;

a sequencer (!06) for sequencing the extracted microbial nucleic acid content, via a sequencer, to get sequence data;

one or more hardware processors;

a memory in communication with the one or more hardware processors, wherein the one or more first hardware processors are configured to execute programmed instructions stored in the one or more first memories, to:

categorize the sequenced data into a plurality of taxonomic groups utilizing standardized classification algorithms and a plurality of databases;

compute raw abundance values of a plurality of features, wherein each feature corresponds to a unique taxonomic group from amongst the plurality of taxonomic groups;

normalize and scale the computed raw abundance values of each of the plurality of features, wherein the normalizing is configured to adjust the raw abundance values to a common scale, thereby correcting a bias in the computation of the raw abundance values, wherein the bias is due to a plurality of factors;

identify a set of features from the plurality of features based on similarity between a nucleotide sequence corresponding to the feature and the nucleotide sequences corresponding to a set of pre-identified amplicon sequence variants (ASVs), and wherein the set of features is identified if the similarity exceeds a pre-defined range;

perform one or more feature engineering techniques on the normalized and scaled abundance values of the set of features to obtain a collated feature table (CFT), wherein the CFT comprises of a plurality of novel engineered features and their corresponding engineered raw abundance values;

provide binary classifier utilizing a pre-built classification model;

compute a mosquito attractiveness quotient (MAQ) score by feeding the CFT to the binary classifier; and compare the computed MAQ score with a predefined threshold score, to categorize the individual to be one of a highly attractive or a poorly attractive to mosquitoes; and an administration module for administering skin microbe based therapeutic interventions to the individual, if the individual is categorized as highly attractive to mosquitoes, wherein the therapeutic interventions are configured to:

combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

14. One or more non-transitory machine-readable information storage mediums comprising one or more instructions which when executed by one or more hardware processors cause:

collecting a biological sample from skin of the individual, wherein the biological sample is representing skin microbiome of the individual;

extracting, via an extraction unit, microbial nucleic acid content from the collected biological sample;

sequencing the extracted microbial nucleic acid content, via a sequencer, to get sequence data;

categorizing, the sequenced data into a plurality of taxonomic groups utilizing standardized classification algorithms and a plurality of databases;

computing, via the one or more hardware processors, raw abundance values of a plurality of features, wherein each feature corresponds to a unique taxonomic group from amongst the plurality of taxonomic groups;

normalizing and scaling, via the one or more hardware processors, the computed raw abundance values of each of the plurality of features, wherein the normalizing is configured to adjust the raw abundance values to a common scale, thereby correcting a bias in the computation of the raw abundance values, wherein the bias is due to a plurality of factors;

identifying, via the one or more hardware processors, a set of features amongst the plurality of features based on similarity between a nucleotide sequence corresponding to the feature and the nucleotide sequences corresponding to a set of pre-identified amplicon sequence variants (ASVs), and wherein the set of features is identified if the similarity exceeds a pre-defined range;

performing, via the one or more hardware processors, one or more feature engineering techniques on the normalized and scaled abundance values of the set of features to obtain a collated feature table (CFT), wherein the CFT comprises of a plurality of novel engineered features and their corresponding engineered abundance values;

providing, via the one or more hardware processors, a binary classifier, wherein the binary classifier utilizing a pre-built classification model;

computing, via the one or more hardware processors, a mosquito attractiveness quotient (MAQ) score by feeding the CFT to the binary classifier;

comparing, via the one or more hardware processors, the computed MAQ score with a predefined threshold score, to categorize the individual to be one of a highly attractive or a poorly attractive to mosquitoes; and administering, via an administration module, skin microbe based therapeutic interventions to the individual, if the individual is categorized as highly attractive to mosquitoes, wherein the therapeutic interventions are configured to:

combat the growth of bacterial groups that metabolize/bio-synthesize sweat and metabolic compounds that are responsible for the production of skin odor that makes the individual attractive to mosquitoes, aid in the colonization of bacterial groups that improve skin-barrier function and maintain skin health, aid in degradation of sweat and metabolic compounds that are responsible for the production of skin odor that makes the individual attractive to mosquitoes, or bio-synthesize sweat and metabolic compounds that are responsible for production of skin odor that makes the individual less attractive to mosquitoes.

* * * * *

SEQUENCE LISTING

```
<160> NUMBER OF SEQ ID NOS: 8

<210> SEQ ID NO 1
<211> LENGTH: 199
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to strains belonging to Staphylococcus
      capitis and Staphylococcus caprae

<400> SEQUENCE: 1
ctggaccgtg tctcagttcc agtgtggccg atcaccctct caggtcggct acgcatcgtt      60
gccttggtaa gccgttacct taccaactag ctaatgcggc gcggatccat ctataagtga     120
cagcaagacc gtctttcact gttgaaccat gcggttcaac atgttatccg gtattagctc     180
cggttcccga agttatccc                                                  199

<210> SEQ ID NO 2
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to Corynebacterium tuberculostearicum
      strain Medalle X and Corynebacterium tuberculostearicum strain
      ATCC

<400> SEQUENCE: 2
ctgggccgta tctcagtccc aatgtggccg tccaccctct caggccggct accgtcgcc       60
```

```
gccttggtag gccattaccc caccaacaag ctgataggcc gcgagctcat cctacaccga    120
aaaaactttc caaccatcac actaaaaatg gttcctatcc ggtattagac ccagtttccc    180
aggcttatcc cgaagtgcag                                                200
```

<210> SEQ ID NO 3
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to Pelomonas puraquae strain Ps10g

<400> SEQUENCE: 3

```
ctgggccgtg tctcagtccc agtgtggctg gtcgtcctct cagaccagct acagatcgtc    60
ggcttggtga gccttaccct caccaactac ctaatctgat atcggccgct ccaatcgcgc    120
gaggtcttgc gatcccccgc tttcaccctc aggtcgtatg cggtattagc tgctctttcg    180
agcagttatc ccccacgact                                                200
```

<210> SEQ ID NO 4
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to multiple species/strains belonging
      to genus Bradyrhizobium

<400> SEQUENCE: 4

```
ttgggccgtg tctcagtccc aatgtggctg atcatcctct cagaccagct actgatcgtc    60
gccttggtag gccattaccc taccaactag ctaatcagac gcgggccgat ctttcggcga    120
taaatctttc cccgtaaggg cttatccggt attagcacaa gtttccctgt gttgttccga    180
accaaaaggt acgttcccac                                                200
```

<210> SEQ ID NO 5
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to Roseateles aquatilis strain CCUG
      48205

<400> SEQUENCE: 5

```
ctgggccgtg tctcagtccc agtgtggctg gtcgtcctct cagaccagct acagatcgtc    60
ggcttggtag gcctttaccc caccaactac ctaatctgat atcggccgct ccaatcgcgc    120
gaggtccgaa gatcccccgc tttcaccctc aggtcgtatg cggtattagc tgctctttcg    180
agcagttatc ccccacgact                                                200
```

<210> SEQ ID NO 6
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to Bradyrhizobium elkanii strain USDA
      76

```
<400> SEQUENCE: 6
ctgggccgtg tctcagtccc agtgtggctg atcatcctct cagaccagct actgatcgtc      60
gccttggtga gccattacct caccaactag ctaatcagac gcgggccgat ctttcggcga     120
taaatctttc cccgttaggg cttatccggt attagctgaa gtttccctca gttgttccga     180
accaaaaggt acgttcccac                                                  200

<210> SEQ ID NO 7
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to strains ATCC 8482 and JCM 5826
      belonging to Bacteroides vulgatus

<400> SEQUENCE: 7
ttggaccgtg tctcagttcc aatgtggggg accttcctct cagaacccct atccatcgaa      60
gactaggtgg gccgttaccc cgcctactat ctaatggaac gcatccccat cgtctaccgg     120
aataccttta atcatgtgaa catgtgaact catgatgcca tcttgtatta atcttccttt     180
cagaaggctg tccaagagta                                                  200

<210> SEQ ID NO 8
<211> LENGTH: 200
<212> TYPE: DNA
<213> ORGANISM: Unknown
<220> FEATURE:
<223> OTHER INFORMATION: Amplicon Sequence Variant (ASV) having >= 99%
      sequence identity (with 100% coverage and BLAST e-value <= 1e-5)
      to sequences corresponding to Roseateles aquatilis strain CCUG
      48205

<400> SEQUENCE: 8
ctgggccgtg tctcagtccc agtgtggctg gtcgtcctct cagaccagct acagatcgtc      60
ggcttggtag gcctttaccc caccaactac ctaatctgat atcggccgct ccaatcgcgc     120
gaggtccgaa gatcccccgc tttcaccctc aggtcgtatg cggtattagc tgctctttcg     180
agcagttatc ccccagactg                                                  200
```